United States Patent [19]  
Cilento et al.

[11] Patent Number: 5,059,189  
[45] Date of Patent: Oct. 22, 1991

[54] METHOD OF PREPARING ADHESIVE DRESSINGS CONTAINING A PHARMACEUTICALLY ACTIVE INGREDIENT

[75] Inventors: Rodolfo D. Cilento, North Brunswick; Margaret A. Frank, Lawrenceville, both of N.J.; John E. Fairbrother, Wales, United Kingdom; Frank M. Freeman, Lawrenceville, N.J.

[73] Assignee: E. R. Squibb & Sons, Inc., Princeton, N.J.

[21] Appl. No.: 94,364

[22] Filed: Sep. 8, 1987

[51] Int. Cl.$^5$ .............................................. A61F 13/02
[52] U.S. Cl. .................................... 604/307; 128/156; 156/66; 604/336; 424/449
[58] Field of Search ................. 128/156; 604/304, 307, 604/336; 424/448, 449; 156/66; 514/887

[56] References Cited

U.S. PATENT DOCUMENTS

| | | | |
|---|---|---|---|
| 2,628,187 | 2/1953 | Frohmader et al. | 514/789 |
| 2,628,205 | 2/1953 | Shoemaker | 424/70 |
| 3,339,546 | 9/1967 | Chen | 128/156 |
| 3,598,122 | 8/1971 | Zaffaroni | 424/435 |
| 3,598,123 | 8/1971 | Zaffaroni | 424/435 |
| 3,632,740 | 1/1972 | Robinson et al. | 424/28 |
| 3,699,963 | 10/1972 | Zaffaroni . | |
| 3,731,683 | 5/1973 | Zaffaroni . | |
| 3,734,097 | 5/1973 | Zaffaroni | 424/448 |
| 3,742,951 | 7/1973 | Zaffaroni . | |
| 3,797,494 | 3/1974 | Zaffaroni | 424/434 |
| 3,972,328 | 8/1976 | Chen | 128/156 |
| 3,996,934 | 12/1976 | Zaffaroni . | |
| 4,031,894 | 6/1977 | Urquhart et al. . | |
| 4,192,785 | 3/1980 | Chen et al. | 523/118 |
| 4,286,592 | 9/1981 | Chandrasekaran | 128/156 |
| 4,307,717 | 12/1981 | Hymes et al. | 128/156 |
| 4,409,206 | 10/1983 | Stricker | 424/81 |
| 4,455,146 | 6/1984 | Noda et al. | 424/448 |
| 4,538,603 | 9/1985 | Pawelchak et al. | 128/156 |
| 4,551,490 | 11/1985 | Doyle et al. | 524/22 |
| 4,568,343 | 2/1986 | Leeper et al. | 424/449 |
| 4,573,995 | 3/1986 | Chen et al. | 424/449 |
| 4,623,346 | 11/1986 | von Bittera et al. . | |
| 4,627,852 | 12/1986 | von Bittera et al. . | |
| 4,643,180 | 2/1987 | Feld et al. | 128/156 |
| 4,668,232 | 5/1987 | Cordes et al. . | |
| 4,675,009 | 6/1987 | Hymes et al. | 604/304 |
| 4,695,465 | 9/1987 | Kigasawa et al. | 424/449 |

FOREIGN PATENT DOCUMENTS 272149 6/1988 European Pat. Off. .
2073588 10/1981 United Kingdom .

Primary Examiner—David J. Isabella
Assistant Examiner—Paul Prebilic
Attorney, Agent, or Firm—Richard H. Brink; Stephen B. Davis

[57] ABSTRACT

A dressing comprising a flexible backing member and a pressure sensitive adhesive layer. The adhesive layer comprises one or more polyisobutylenes, elastomers, and one or more moisture absorbing, moisture transmitting, water soluble and/or water swellable agents. A dispersion of the active ingredient in a medium compatible with the adhesive layer is laminated to the skin contacting surface.

12 Claims, No Drawings

METHOD OF PREPARING ADHESIVE DRESSINGS CONTAINING A PHARMACEUTICALLY ACTIVE INGREDIENT

BACKGROUND OF THE INVENTION

Chen in U.S. Pat. No. 3,339,546 disclose a bandage capable of adhering to moist body surfaces comprising a polymeric film and an adhesive layer. The adhesive layer comprises one or more water soluble or swellable hydrocolloids such as pectin, gelatin, carboxymethylcellulose, etc., dispersed in a natural or viscous gum like substance such as natural rubber, silicone rubber, acrylonitrile rubber, or polyisobutylene which is preferred. Chen discloses applying a medicament such as an antibiotic, an anesthetic, or an anti-inflammatory agent by dusting, spraying or coating onto the adhesive surface or by incorporating the medicament within the adhesive composition.

Doyle et al. in U.S. Pat. No. 4,551,490 disclose medicinal grade pressure sensitive adhesive compositions comprising a homogeneous mixture of one or more polyisobutylenes or blends of one or more polyisobutylenes and butyl rubber, one or more styrene radial or block type copolymers, mineral oil, one or more water soluble hydrocolloid gums, and a tackifier. One or more water soluble cohesive strengthening agents, an antioxidant, and various other optional ingredients including pharmaceutically active agents such as antibiotics, antimicrobial agents, antiseptics, and anti-inflammatory agents can be included within the adhesive composition.

Robinson et al. in U.S. Pat. No. 3,632,740 disclose increasing the effectiveness of topical corticosteroids by dispersing the corticosteroid through a pressure sensitive adhesive which is then adhered to the skin in the form of a thin film. Acrylic type pressure sensitive adhesives are preferred though polyisobutylene and natural rubber are also employed. The corticosteroid is dispersed throughout the entire pressure sensitive adhesive by dissolving in solvent which is blended into the adhesive and then evaporated. The adhesive has a conventional backing such as woven or nonwoven fabrics, paper, and polymeric films.

Hymes et al. in U.S. Pat. No. 4,307,717 disclose an adhesive bandage containing a medicament. The bandage comprises a flexible backing and a hydrophilic adhesive matrix comprising about 30 to 50% of polyacrylic acid, polyacrylamide and their cogeners and a liquid phase consisting of a solution or emulsion of carbohydrate and/or protein, and a medicament such as an anti-inflammatory agent. The solid phase of the matrix can include a gum such as karagen, gum acacia, locust bean gum, and guar gum.

Noda et al. in U.S. Pat. No. 4,455,146 disclose plasters comprising a thermoplastic elastomer such as a styrene-isoprene-styrene TR block copolymer, an oil or higher fatty acid, a tackifier, and a medicinal ingredient such as a topical steroid.

Feld et al. in U.S. Pat. No. 4,643,180 disclose antimicrobial adhesive surgical dressing. The antimicrobial agent, polyhexamethylene biguanide, is applied to the surface of the adhesive to a depth of not more than about 50% of the thickness of the adhesive.

Zaffaroni in U.S. Pat. No. 3,598,122 discloses a bandage for use in the continuous administration of systemically active drugs by absorption through the skin or oral mucosa. The bandage consists of a drug reservoir which is a hollow drug container or a solid or gel matrix. The drug is trapped within the container or the drug is added to the matrix material in liquid form and subsequently the matrix is converted to a solid by curing or cooling or by immersing the solid matrix in the drug to effect diffusion. One surface of the reservoir bears a backing member and the other has a layer of pressure sensitive adhesive. Suitable adhesive materials include the acrylic type, rubbery polymers such as polyisobutylene, and natural gums such as guar, acacia, pectin, etc. The adhesive layer can include tackifier and stabilizers. In use, drug molecules are continuously removed from the outer surface of the reservoir through the adhesive layer to the outer skin contacting surface where they are absorbed by the skin.

Eaffaroni in U.S. Pat. No. 3,598,123 also discloses a bandage for use in the continuous administration of systemically active drugs by absorption through the skin or oral mucosa. The bandage consists of a backing member having a pressure sensitive adhesive on one surface. The pressure sensitive adhesive has microcapsules of a systemically active drug encapsulated with a material permeable to passage of the drug distributed therethrough. The adhesive material is described similarly to 3,598,122.

Zaffaroni in U.S. Pat. No. 3,699,963 discloses a therapeutic adhesive patch for administering an oxytocic drug through the oral mucosa to stimulate uterine contractions. The patch consists of a flexible backing and a presure sensitive adhesive in which the oxytocic drug is mixed. Alternatively, a solution or suspension of the drug can be sprayed on the adhesive surface of the patch. Other embodiments show the drug microcapsulated or within a drug microcapsulated or within a reservoir. Again, the pressure sensitive adhesive layer is described similarly to 3,598,122.

Zaffaroni in U.S. Pat. No. 3,731,683 discloses a bandage for continuous administration of topically active drugs to the skin. The bandage consists of a flexible or non-flexible backing member which can be occlusive or non-occlusive and a pressure sensitive adhesive layer which contacts the skin. The drug can be microcapsulated and the microcapsules distributed throughout the adhesive layer. Alternatively, the drug can be within a discrete middle reservoir layer having a wall formed from drug release rate controlling material permeable to the active agent. Again, the pressure sensitive adhesive is defined similarly to 3,598,122.

Zaffaroni in U.S. Pat. No. 3,734,097 describes a therapeutic adhesive tape similar to that in U.S. Pat. No. 3,731,683 particularly adapted for treating skin lesions wherein the active ingredient is an anti-neoplastic agent or a folic acid antagonist. A similar bandage for the controlled release of vasodilators is described by Zaffaroni in U.S. Pat. No. 3,742,951. A similar non-adhesive medical bandage is described by Zaffaroni in U.S. Pat. No. 3,996,934.

Zaffaroni in U.S. Pat. No. 3,797,494 describes a bandage for administration of topical or systemic drugs by controlled metering through microporous material. The bandage can include a backing member, a reservoir layer containing the drug confined within a body formed from drug release rate controlling microporous material permeable to the passage of the drug, and a pressure-sensitive adhesive layer. Alternatively, the reservoir is formed of material permeable to passage of the drug and one or more drug release rate controlling microporous membranes are interposed between the reservoir and the adhesive. In another embodiment, the adhesive layer itself contains a plurality of discrete microcapsules each of which contains the drug within a body of drug release rate controlling porous material.

Urquhart et al. in U.S. Pat. No. 4,031,894 describe a bandage for transdermally administering scopolamine to prevent nausea. The bandage consists of a backing, a gelled, mineral oil-polyisobutylenescopolamine reservoir, a microporous rate controlling membrane, and a gelled, mineral oil-polyisobutylenescopolamine adhesive layer.

von Bittera et al. in U.S. Pat. Nos. 4,623,346 and 4,627,852 disclose a medicinal plaster comprising a covering layer which is essentially impermeable to the active compound, an active compound reservoir, and a protective layer which can be pulled off and is essentially impermeable to the active compound. The reservoir in 4,623,346 contains 1-30% of active compound, 30-60% of polyisobutylene or copolymers of polyisobutylene, 30-60% of an entraining agent such as paraffin oil, mineral oil, etc., and 2-40% of a tackifier. The reservoir in 4,627,852 contains 1-30% of active compound in a elastomer mixture comprising a diene rubber which can be randomly copolymerized with an α-olefin, up to 70% of polyisobutylene, polybutadiene, and/or paraffin oil, and a tackifier.

Stricker in U.S. Pat. No. 4,409,206 discloses a transdermal film release system comprising a polyacrylate that swells in water and a pharmaceutically active substance in amorphous form. The polyacrylate dispersion can also contain hydrophilic auxiliary substances such as polyethylene glycol, glycerin, sorbitol, or mixtures thereof to regulate the rate of release of the pharmaceutical.

Cordes et al. in U.S. Pat. No. 4,668,232 disclose a transdermal drug patch comprising an impermeable backing layer, a reservoir layer, and an adhesive layer. The reservoir comprises a polymer matrix composed of a rubber such as polyisobutylene and an adhesive resin material in which a therapeutically active drug is present in wholly or partially soluble form and a polymer capable of swelling in water and insoluble in the rubber and adhesive resin material of the reservoir layer.

SUMMARY OF THE INVENTION

This invention is directed to a pressure sensitive, adhesive dressing containing a pharmaceutically active ingredient and to the method of preparing such dressing. The adhesive layer of the dressing is capable of releasing the active ingredient to the surface of the skin covered by the dressing over a period of time of from several hours to one or more days. The surface of the adhesive layer opposite the skin contacting surface is attached to a flexible backing member.

The adhesive layer comprises a homogeneous blend of one or more polyisobutylenes or mixture of one or more polyisobutylenes and an elastomer such as butyl rubber and/or styrene radial or block type copolymers and one or more moisture absorbing, moisture transmitting, water soluble or water swellable agents. The adhesive may contain other optional ingredients such as mineral oil, tackifiers, antioxidants, etc.

The pharmaceutically active ingredient is incorporated into the adhesive layer so that it resides at the skin contacting surface and in the strata of the adhesive layer closest to the skin contacting surface. This is accomplished by forming a suspension of the active ingredient in a material which is compatible with the composition of the adhesive layer. This suspension is then cast onto a sheet of silicone coated release paper which is then laminated to the skin contacting surface of the adhesive layer.

DETAILED DESCRIPTION OF THE INVENTION

The pressure sensitive adhesive dressing of this invention consists of an adhesive layer formulated from materials suitable for use on human skin and a flexible backing layer. The adhesive layer must be capable of bonding to the skin for from several hours to several days.

Suitable pressure sensitive adhesive compositions for use as the skin contacting adhesive layer of the dressing of this invention are homogeneous blends of one or more polyisobutylenes or mixtures of one or more polyisobutylenes and an elastomer such as butyl rubber, medium or high molecular weight polyisobutylene and/or styrene radial or block type copolymers and one or more moisture absorbing, moisture transmitting, water soluble and/or water swellable agents. The adhesive compositions may contain other optional ingredients such as mineral oil, tackifiers, antioxidants, etc.

The polyisobutylene component of the pressure sensitive adhesive compositions function to provide adhesion to dry body surfaces, i.e., dry tack, and along with the flexible backing layer maintain the structural integrity of the dressing. Preferably, the polyisobutylenes employed are one or more low molecular weight polyisobutylenes having a viscosity average molecular weight of from about 8,700 to about 1,700 (Staudinger). Such polyisobutylenes are commercially available under the trademark VISTANEX from Exxon as grades LM - MS and LM - MH.

The polyisobutylene can be combined with one or more elastomers. These materials function to increase the elasticity, tear resistance, and cohesiveness of the adhesive compositions. Suitable elastomers include butyl rubber which is a copolymer of isobutylene with a minor amount of isoprene having a viscosity average molecular weight of from about 350,000 to about 50,000 (Florey), medium and high molecular weight polyisobutylene such as VISTANEX MM L-100 having a viscosity average molecular weight of from about 81,000 to about 99,000 (Staudinger) and styrene radial or block copolymers. Particularly suitable styrene copolymers include styrene-butadiene-styrene (S-B-S) and styrene-isoprene-styrene (S-I-S) block type copolymers both of which are commercially available, for example, from Shell Chemical Co. under their tradename KRATON 1100, 1101, 1102, 1107, etc.

The moisture absorbing, moisture transmitting, water soluble or water swellable agents permit the adhesive compositions to adhere to moist body surfaces, i.e., wet tack. In addition, while not being limited in attempting to explain the mechanism by which the pharmaceutical ingredient is released from the dressing, it is believed that the absorption of moisture from the surface of the skin into the adhesive layer results in a dynamic change in the microenvironment at the adhesive layer-skin interface caused by hydration of these agents at the adhesive surface and gradually throughout the entire adhesive layers. This results in the continuous release of the topically active pharmaceutical agent from the adhesive layer. Suitable water soluble agents for incorporation within the adhesive compositions are hydrocolloid gums including sodium carboxymethylcellulose, potassium carboxymethylcellulose, pectin, gelatin, guar gum, locust bean gum, gum karaya, xanthan gum, mixed sodium/calcium salts of alginic acid, carrageenan, etc., and mixtures thereof. Suitable water swellable agents include substantially water insoluble cross-linked sodium carboxymethylcellulose such as that commercially available under the trademarks AcDiSol or Aqualon or that described in U.S. Pat. No. 3,589,364, substantially water insoluble starch-acrylonitrile graft copolymer such as that in U.S. Pat. No. 3,661,815 and that commercially available from Grain Processing Corp. under their Water-Lock trademark, and substantially water insoluble cross-linked dextran such as that commercially available under the trademark Sephadex.

Mineral oil can be included within the adhesive layer both as a component of the pressure sensitive adhesive formulation and, as explained below, as the preferred agent for incorporating or depositing the pharmaceutically active agent at the skin contacting surface and in the strata of the adhesive layer closest to the skin contacting surface. Tackifiers can also be included within the adhesive layer. Suitable tackifiers include the pentaerythritol esters of rosin commercially available from Hercules under the trademark PENTALYN H, trimethylol propane ester of rosin commercially available from Hercules under the tradename Staybelite Ester 10, and the beta pinine resins such as Piccolyte S115 or the cyclopentadiene resins commercially available from Exxon such as ESCOREZ 5300 or the Arakawa cyclic tackifiers namely the Arkon products. The adhesive layer can also contain small amounts, i.e., less than about 2% by weight of an antioxidant such as zinc dibutyldithiocarbamate (commercially available from R. T. Vanderbilt Co. under the tradename BUTYL ZIMATE) or those available from Ciba Geigy such as IRGANOX 1010, tetrakis [methylene(3,5-ditert-butyl-4-hydroxyhydrocinnamate] or Irganox 1076, octadecyl 3-[3,5-ditert-butyl-4'-hydroxy-phenyl]propionate, etc.

The thickness of the adhesive layer can be varied. In general, the adhesive layer will be from about 20 to about 100 mils. Thicknesses greater than 100 mils are undesirable as being uncomfortable to wear and more prone to accidental removal.

Preferably, the composition of the adhesive layer prior to incorporation of the pharmaceutically active ingredient contains from about 15% to about 50% by weight of polyisobutylenes or blends of polyisobutylenes and one or more elastomers, from about 20% to about 70% by weight of one or more moisture absorbing, moisture transmitting, water soluble and/or water swellable agents, up to about 25% by weight of mineral oil, and up to about 20% by weight of tackifiers.

The surface of the adhesive layer that does not contact the skin has a flexible backing member affixed to it. Suitable backing members include polymeric films, woven and nonwoven fabric backings, and polymeric foams which themselves have a film or skin on the outer surface opposite the adhesive layer. Suitable commercially available polymeric films include films made from polyethylene, polyurethane, polyether polyamide block copolymers, etc. Suitable commercially available nonwoven fabric backings include materials made from polyester fibers, polypropylene fibers, nylon fibers, composite olefin fibers, or cellulosic fibers. Suitable woven fabric backings include cotton, cotton blends, etc. Suitable polymeric foams include semi-open cell polyurethane foam as described by Chen in U.S. Pat. No. 3,972,328. The skin contacting pressure sensitive adhesive layer can be affixed to the polyurethane foam by means of a secondary adhesive layer as taught by Pawelchak et al. in U.S. Pat. No. 4,538,603.

When the flexible backing member is a polymeric film or fabric, it will vary in thickness from about 1 to about 5 mils. When the flexible backing member is a polymeric foam, it will vary in thickness from about 20 to about 100 mils.

The pharmaceutically active ingredient is incorporated into the adhesive layer so that it resides at the skin contacting surface and in the strata of the adhesive layer closest to the skin contacting surface. This is accomplished by forming a suspension of the pharmaceutically active ingredient in a material or medium which is compatible with the composition of the adhesive layer, i.e., able to be absorbed or intermixed or dissolved in the surface of the adhesive layer without impairing its adhesive characteristics. Of course, this material must be inert with respect to the active ingredient and capable of dispersing or dissolving it. This material must also be non-irritating, non-sensitizing, non-allergenic, and non-toxic. The resulting suspension is then cast onto a sheet of silicone coated release paper which is laminated to the skin contacting surface of the adhesive layer.

Various classes of pharmaceutically active ingredients can be incorporated into the dressing of this invention. Among the classes are topical anti-inflammatory agents and antipruritics including steroids such as triamcinolone acetonide, halcinonide, betamethasone valerate, hydrocortisone, tipredane, etc., and non-steroidal agents such as bufexamac, camphor, aspirin, etc., antipsoriatrics such as dithranol, coal tar extracts, etc., keratolytics such as salicylic acid, urea, etc., local anaesthetics such as lidocaine, benzocaine, etc., antibacterials such as benzalkonium chloride, fusidic acid, chlorhexidine, etc. antifungals such as nystatin, dithranol, amphotericin, econazole, etc., anti-viral agents, anti-acne agents such as benzoyl peroxide, vitamin A derivatives, etc., biological factors such as urokinase, tissue plaminogen activator, angiogenesis factor, etc., wart removers such as salicylic acid, lactic acid, etc., and enzymes such as fibrinolytic or proteolytic enzymes.

The preferred material for forming the suspension of the active ingredient is mineral oil and particularly mineral oil thickened by mixing with a polyethylene and liquid petrolatum base, i.e., PLASTIBASE, the mineral oil and PLASTIBASE being mixed on a 1:1 basis. The active ingredient is suspended in the mineral oil in an amount up to about 15% by weight with about 10% by weight being preferred. Other agents such as surfactants, suspending agents, skin penetration enhancers, thickeners, etc., can optionally be added in small quantities to the suspension.

The adhesive layer can also contain various optional ingredients. For example, the adhesive layer can contain up to about 10% by weight of the pharmaceutically active ingredient blended directly into the mixture of polyisobutylenes, elastomers, water soluble and/or water swellable agents. While such blended pharmaceutically active material is not released from the adhesive layer in an amount and at a rate to be useful by itself, it is released in a sufficient amount to augment the release of the pharmaceutically active material contained at and adjacent the skin contacting surface of the adhesive layer. Alternatively, the dressing can include a reservoir containing the pharmaceutically active material as described, for example, in the Zaffaroni patents and this reservoir can be employed to augment the release of the pharmaceutically active material contained at and adjacent the surface of the adhesive layer. In addition, the adhesive layer can contain up to about 10% by weight of one or more agents to enhance the penetration of the pharmaceutically active agent into the skin of the user. Suitable penetration enhancers include oleic acid and other unsaturated acids, methyl-2-pyrrolidone, 2-pyrrolidone, lactic acid, phosphatidol choline and other phospholipids, dimethylisosorbide, dimethyl sulfoxide, Azone, etc.

The pharmaceutically active adhesive dressings of this invention can be prepared as follows. The process will vary somewhat depending upon the particular polyisobutylenes and/or mixtures of polyisobutylenes and elastomers employed in the adhesive layer. However, in general, these viscous materials along with the mineral oil and tackifiers are combined and blended in a sigma blade type mixer at room temperature or with heating. A blend of the powdery water soluble or swellable agents along with any other optional ingredients are added gradually and mixing is continued until a homogeneous mass is obtained as described in the Doyle et al. and Pawelchak et al. patents discussed above. The adhesive mass is layered onto a sheet of silicone coated release paper, flattened to the desired thickness by either calendering or extruding, and a flexible backing member is laminated to the other surface of the adhesive layer.

A dispersion or suspension of the pharmaceutically active ingredient in a medium compatible with the adhesive layer is formed. This dispersion is cast onto a sheet of silicone coated release paper as a thin uniform layer using a knife-over-roller, Meyer Rods, a transfer roll coater, etc. The release paper is stripped off the adhesive layer and the adhesive layer is laminated to the silicone release paper coated with the dispersion of the pharmaceutically active material.

The adhesive dressings of this invention can be sterilized by means of gamma radiation.

The following examples are illustrative of the invention.

EXAMPLE 1

A pressure sensitive adhesive is prepared consisting of the following ingredients:

| Ingredient | Weight percent within the adhesive mass |
| --- | --- |
| Polyisobutylene (VISTANEX LM-MH) | 8 |
| Styrene-isoprene-styrene copolymer (KRATON D1107) | 6 |
| Butyl rubber (Grade 065-EXXON) | 16.25 |
| Tackifier (Pentalyn H) | 12.75 |
| Mineral oil | 11.50 |
| Antioxidant (IRGANOX 1010) | 0.50 |
| Sodium carboxymethylcellulose | 15.00 |
| Pectin | 15.00 |
| Gelatin | 15.00 |

The mineral oil (40.83 kg.), polyisobutylene (28.40 kg.), KRATON D1107 (21.30 kg.), IRGANOX 1010 (1.80 kg.) and butyl rubber (57.68 kg.) are combined in a sigma blade mixer with heating (about 115° C.) and agitating for approximately 1 to 2.5 hours. The mixture is cooled to about 100° C. and after another 30 minutes of blending, sodium carboxymethylcellulose (53.25 kg.), pectin (53.25 kg.), gelatin (53.25 kg.), and PENTALYN H (45.26 kg.) are added. Mixing is continued at about 100° C. for 30 minutes to give 355 kg. of a homogeneous adhesive mass.

The mass is allowed to cool and is flattened into an adhesive layer of the desired thickness of about 35 mils. A sheet of polyethylene is laminated to one surface and silicone coated release paper to the other.

Powdered triamcinolone acetonide ( 10 0 g.) is dispersed in a mixture of mineral oil and PLASTIBASE 50W at a 1:1 ratio (90.0 g). The dispersion is cast onto silicone coated release paper by means of a Meyer rod (#2) to give a uniform layer of dispersion of 7 to 8 mg./in.$^2$.

The release paper is removed from the adhesive layer and this layer is laminated on the triamcinolone acetonide dispersion layer. In a few hours the dispersion is absorbed into the adhesive surface creating a smooth, glossy, tacky surface.

The resulting dressing contains at its surface 0.75 mg./in.$^2$ of triamcinolone acetonide.

EXAMPLE 2

Following the procedure of Example 1 but dispersing ( 2 g.) of triamcinolone acetonide in the thickened mineral oil, the resulting dressing contains 0.15 mg./in.$^2$ of triamcinolone acetonide at its surface.

EXAMPLE 3

A pressure sensitive adhesive is prepared consisting of the following ingredients:

| Ingredient | Weight percent within the adhesive mass |
| --- | --- |
| Polyisobutylene (VISTANEX LM-MH) | 9.55 |
| Styrene-isoprene-styrene copolymer (KRATON D1107) | 20.55 |
| Tackifier (PENTALYN H) | 12.80 |
| Mineral oil | 20.45 |
| Antioxideant (IRGANOX 1010) | 1.55 |
| Sodium carboxymethylcellulose | 25.70 |
| Cross-linked sodium carboxymethylcellulose (Ac-DiSol) | 9.40 |

The mineral oil (22.5 kg.), polyisobutylene (10.5 kg.), KEATON D1107 (22.6 kg.), and IRGANOX 1010 (1.7 kg.) are combined in a sigma blade mixer with heating (about 115° C.) and agitating for approximately 1 to 2.5 hours. After cooling with additional blending, the sodium carboxymethylcellulose (28.3 kg.), Ac-Di-Sol (10.3 kg.), and PENTALYN H (14.1 kg.) are added. Mixing is continued at about 100° C. for 30 minutes to give 110 kg. of a homogeneous adhesive mass.

The adhesive mass is allowed to cool and is flattened into an adhesive layer of the desired thickness of about 35 mils. A sheet of polyethylene is laminated to one surface and the triamcinolone acetonide-mineral oil dispersion described in Example 1 is laminated to the other adhesive surface.

The resulting dressing contains 0.75 mg./in.$^2$ of triamcinolone acetonide at the adhesive surface.

EXAMPLE 4

Following the procedure of Example 3 but employing the triamcinolone acetonide-mineral oil dispersion of Example 2, a dressing is obtained containing 0.15 mg./in.$^2$ of triamcinolone acetonide at the adhesive surface.

EXAMPLE 5

A pressure sensitive adhesive is prepared consisting of the following ingredients:

| Ingredient | Weight percent within the adhesive mass |
|---|---|
| Polyisobutylene (VISTANEX LM-MH) | 9.5 |
| Polyisobutylene (VISTANEX MM-L100) | 9.5 |
| Mineral oil | 14.4 |
| Sodium carboxymethyl-cellulose | 22.2 |
| Pectin | 22.2 |
| Gelatin | 22.2 |

The VISTANEX MM-L100 (5.7 kg.) is added to the mixer and agitated for several minutes. The VISTANEX LM-MH (5.7 kg.) is added and mixing continued for about 5 minutes. The gelatin is then added (13.3 kg.) and mixing continued for another 5 minutes. This is followed by addition of the mineral oil (8.7 kg.) over a period of several minutes followed by the sodium carboxymethylcellulose (13.3 kg.) and pectin (13.3 kg.). Mixing is continued for another 20 minutes to give 60 kg. of a homogeneous adhesive mass.

The adhesive mass is flattened into an adhesive layer of the desired thickness of about 35 mils. A sheet of polyethylene is laminated to one surface and the triamcinolone acetonide-mineral oil dispersion described in Example 1 is laminated to the other adhesive surface.

The resulting dressing contains 0.75 mg./in.$^2$ of triamcinolone acetonide at the adhesive surface.

EXAMPLE 6

Following the procedure of Example 5 but g the triamcinolone acetonide-mineral oil dispersion of Example 2, a dressing is obtained containing 0.15 mg./in.$^2$ of triamcinolone acetonide at the adhesive surface.

EXAMPLE 7

An adhesive dressing is prepared as described by Pawelchak et al. in Example 1 of U.S. Pat. No. 4,538,603.

The dressing consists of a layer of open cell polyurethane foam of about 0.045 inches thickness having a skin formed on one surface and an adhesive layer of about 0.005 inches on the other surface.

This adhesive layer consists of:

| Ingredient | Percent by weight in the adhesive layer |
|---|---|
| Polyisobutylene (VISTANEX LM-MH) | 18.0 |
| Polyisobutylene (VISTANEX MM L-100) | 20.0 |
| Tackifier (Piccolyte) | 20.0 |
| Antioxidant (BHT) | 0.5 |
| Mineral oil | 8.5 |
| Sodium carboxymethyl-cellulose | 18.00 |
| Gelatin | 15.0 |

A skin contacting adhesive layer of 0.04 inches thickness is laminated to the adhesive layer described above. The skin contacting adhesive layer consists of:

| Ingredient | Percent by weight in the skin contacting adhesive layer |
|---|---|
| Polyisobutylene (VISTANEX LM-MH) | 40 |
| Pectin | 20 |
| Gelatin | 20 |
| Sodium carboxymethyl-cellulose | 20 |

The triamcinolone acetonide—mineral dispersion described in Example 1 is laminated to the skin contacting adhesive layer to give a dressing containing 0.75 mg./in.$^2$ of triamcinolone acetonide at the adhesive surface.

EXAMPLE 8

Following the procedure of Example 7 but employing the triamcinolone acetonide-mineral oil dispersion described in Example 2, a dressing is obtained containing 0.15 mg./in.$^2$ of triamcinole acetonide at the adhesive surface.

EXAMPLE 9

Following the procedure of Example 1 but replacing the triamcinolone acetonide with betamethasone valerate at a concentration of 0.1 mg. per 5.5 mg. of mineral oil-PLASTIBASE-betamethasone valerate mixture and 1.0 mg. per 5.5 mg. of mineral oil-PLASTIBASE-betamethasone valerate mixture to give dressings having from about 0.075 to 0.093 mg./in$^2$. and from about 0.85 to 1.0 mg./in$^2$. of betamethasone valerate at the adhesive surface.

EXAMPLE 10

Following the procedure of Example 1 but replacing the triamcinolone acetonide with dithranol at a concentration of 0.1 mg. per 5.5 mg. of mineral oil-PLASTIBASE-dithranol mixture and 1.0 mg. per 5.5 mg. of mineral oil-PLASTIBASE-dithranol mixture to give dressings having 0.075 mg./in$^2$. and 0.95 mg./in$^2$. of dithranol at the adhesive surface.

EXAMPLES 11–17

Following the procedures of Examples 1 to 10, pressure sensitive adhesive layers are formed of the following ingredients and a pharmaceutically active agent dispersed in thickened mineral oil is laminated to the skin contacting adhesive surface at varying concentrations.

| Ingredient | EXAMPLE | | | | | | |
| | 11 | 12 | 13 | 14 | 15 | 16 | 17 |
|---|---|---|---|---|---|---|---|
| Polyisobutylene (VISTANEX LM-MH) | 10.2 | 8.0 | 20.0 | 35.0 | 10.0 | 10.0 | 30.0 |
| Polyisobutylene (VISTANEX MM-L100) | — | — | 20.0 | — | — | — | — |
| Butyl rubber | — | 16.25 | — | — | — | 15.0 | 10.0 |

-continued

| Ingredient | EXAMPLE | | | | | | |
|---|---|---|---|---|---|---|---|
| | 11 | 12 | 13 | 14 | 15 | 16 | 17 |
| Styrene-isoprene styrene copolymer (KRATON D1107) | 12.6 | 6.0 | — | — | 15.0 | 8.0 | — |
| Tackifier | 8.95 | 12.75 | 20.0 | — | 5.0 | 7.95 | — |
| Mineral Oil | 25.1 | 11.50 | 19.5 | 9.5 | 9.5 | 20.0 | 15.0 |
| Antioxidant | 0.05 | 0.50 | 0.5 | 0.5 | 0.5 | 0.05 | — |
| Sodium carboxymethylcellulose | 31.0 | 20.0 | — | — | 20.0 | 15.0 | — |
| Calcium carboxymethylcellulose | — | — | — | 15.0 | — | — | — |
| Pectin | — | — | — | — | — | 12.0 | — |
| Gelatin | — | — | — | — | — | 12.0 | — |
| Guar gum | — | 15.0 | — | — | 20.0 | — | 20.0 |
| Gum karaya | — | 10.0 | — | — | — | — | — |
| Xanthan gum | — | — | — | 15.0 | — | — | — |
| Mixed Sodium/Calcium alginate | — | — | — | 15.0 | — | — | 15.0 |
| Carrageenan | — | — | — | — | 20.0 | — | — |
| Water insoluble cross-linked sodium carboxymethylcellulose (Ac-Di-Sol) | 12.1 | — | — | — | — | — | — |
| Water insoluble starch-acrylonitrile graft copolymer (WATER LOCK A-100) | — | — | 20.0 | — | — | — | 10.0 |
| Water insoluble cross-linked dextran | — | — | — | 10.0 | — | — | — |
| Concentration of pharmaceutically active ingredient at skin contacting adhesive surface | 0.65 mg/in$^2$ | 0.55 mg/in$^2$ | 0.45 mg/in$^2$ | 0.25 mg/in$^2$ | 0.70 mg/in$^2$ | 0.50 mg/in$^2$ | 0.30 mg/in$^2$ |

What is claimed is:

1. A method of preparing an adhesive dressing containing an pharmaceutically active ingredient comprising:
   a) forming a pressure sensitive adhesive mass comprising:
      i) one or more low molecular weight polyisobutylenes,
      ii) one or more moisture absorbing, moisture transmitting, water soluble and/or water swellable agents, and
      iii) various optical ingredients;
   b) blending said pressure sensitive adhesive mass from step (a) until homogeneous;
   c) layering said blended adhesive mass from step (b) onto a first release coated surface and flattening said mass to form an adhesive layer of desired thickness having a skin contacting surface and an adjacent strata;
   d) laminating a flexible backing member to the exposed surface of said adhesive layer from step (c);
   e) dispersing a pharmaceutically active ingredient into a mineral oil or thickened mineral oil medium which itself is not an adhesive but is compatible with the composition of said skin contacting adhesion layer;
   f) coating or casting said dispersion from step (e) as a uniform layer onto a second release paper; and
   g) removing said first release coated surface from said adhesive layer in step (d) and laminating said coated or cast-on second release paper from step (f) to said adhesive layer so that said dispersion of pharmaceutically active ingredient contacts the now exposed surface of said adhesive layer and is absorbed therein to give an adhesive dressing wherein said pharmaceutically active ingredient is present at both said skin contacting surface and said adjacent strata of said adhesive layer.

2. The process of claim 1 wherein said pressure sensitive adhesive means in step (a) comprises from about 15% to about 50% by weight of one or more low molecular weight polyisobutylenes, from about 20% to about 70% by weight of one or more moisture absorbing, moisture transmitting, water soluble and/or water swellable agents, up to about 25% by weight of mineral oil, and up to about 20% by weight of tackifiers.

3. The process of claim 2 wherein said moisture absorbing, moisture transmitting, water soluble agents are selected from the group consisting of sodium carboxymethylcellulose, calcium carboxymethylcellulose, pectin, gelatin, guar gum, locust bean gum, gum karaya, xanthan gum, mixed sodium/calcium salts of alginic acid, and carrageenan and said moisture absorbing, moisture transmitting water swellable agents are selected from the group consisting of a water insoluble cross-linked sodium carboxymethylcellulose, water insoluble starch acrylonitrile graft copolymers, and water insoluble cross-linked dextran.

4. A method of preparing an adhesive dressing containing a pharmaceutically active ingredient comprising:
   a) forming a pressure sensitive adhesive mass comprising:
      i) one or more low molecular weight polyisobutylenes and one or more elastomers,
      ii) one or more moisture absorbing, moisture transmitting, water soluble and/or water swellable agents, and
      iii) various optical ingredients;
   b) blending said pressure sensitive adhesive mass from step (a) until homogeneous;
   c) layering said blended adhesive mass from step (b) onto a first release coated surface and flattening said mass to form an adhesive layer of desired thickness having a skin contacting adhesive surface and an adjacent strata;
   d) laminating a flexible backing member to the exposed surface of said adhesive layer from step (c);
   e) dispersing a pharmaceutically active ingredient into a mineral oil or thickened mineral oil medium which itself is not an adhesive but is compatible with the composition of said skin contacting adhesive layer;
   f) coating or casting said dispersion from step (e) as a uniform layer onto a second release paper; and g) removing said first release coated surface from said adhesive layer in step (d) and laminating said coated or cast-on second release paper from step (f) to said adhesive layer so that said dispersion of pharmaceutically active ingredient contacts the now exposed surface of said adhesive layer and is absorbed therein to give an adhesive dressing wherein said pharmaceutically active ingredient is present at both said skin contacting surface and said adjacent strata of said adhesive layer.

5. The process of claim 4 wherein said pharmaceutically active ingredient is a topically active anti-inflammatory agent.

6. The process of claim 5 wherein said anti-inflammatory agent is triamcinolone acetonide and said dispersing medium is thickened mineral oil.

7. The process of claim 5 wherein said skin contacting adhesive layer prior to incorporation of the pharmaceutically active ingredient comprises from about 15% to about 50% by weight of blends of one or more low molecular weight polyisobutylenes and one or more elastomers, from about 30% to about 70% by weight of one or more moisture absorbing, moisture transmitting, water soluble and/or water swellable agents, up to about 25% by weight of mineral oil, and up to about 20% by weight of tackifiers.

8. The process of claim 7 wherein said elastomer is selected from the group consisting of butyl rubber, medium and high molecular weight polyisobutylenes, and styrene radial or block copolymers, and said moisture absorbing, moisture transmitting, water soluble agents are selected from the group consisting of sodium carboxymethylcellulose, calcium carboxymethylcellulose, pectin, gelatin, guar gum, locust bean gum, gum karaya, xanthan gum, mixed sodium/calcium salts of alginic acid, and carrageenan and said moisture absorbing, moisture transmitting water swellable agents are selected from the group consisting of a water insoluble cross-linked sodium carboxymethylcellulose, water insoluble starch-acrylonitrile graft copolymers, and water insoluble cross-linked dextran.

9. The process of claim 8 wherein said flexible backing member is selected from the group consisting of polymeric films, woven and nonwoven fabrics, and polymeric foams.

10. The process of claim 1 wherein said pharmaceutically active ingredient is a topically active anti-inflammatory agent.

11. The process of claim 10 wherein said anti-inflammatory agent is triamcinolone acetonide and said dispersing medium is thickened mineral oil.

12. The process of claim 3 wherein said flexible backing member is selected from the group consisting of polymeric films, woven and nonwoven fabrics, and polymeric foams.

* * * * *